United States Patent [19]

Roehm et al.

[11] Patent Number: 5,293,574
[45] Date of Patent: Mar. 8, 1994

[54] DIGITAL X-RAY IMAGING SYSTEM WITH AUTOMATIC TRACKING

[75] Inventors: Steven P. Roehm, Waukesha; James A. Smith, Pewaukee, both of Wis.; Ruchi Mangalik, Buffalo Grove, Ill.

[73] Assignee: General Electric Company, Milwaukee, Wis.

[21] Appl. No.: 965,467

[22] Filed: Oct. 23, 1992

[51] Int. Cl.⁵ .................................................. H05G 1/64
[52] U.S. Cl. ..................................... 378/98.2; 378/62
[58] Field of Search ............... 358/125, 126, 222, 111; 378/99, 98, 62, 43

[56] References Cited

U.S. PATENT DOCUMENTS

| | | | |
|---|---|---|---|
| 4,403,256 | 9/1983 | Green et al. | 358/222 |
| 4,410,914 | 10/1983 | Siau | 358/222 |
| 4,449,195 | 5/1984 | Andrews et al. | 364/900 |
| 4,542,459 | 9/1985 | Riederer | 364/414 |
| 4,559,557 | 12/1985 | Keyes et al. | 358/111 |
| 4,571,619 | 2/1986 | Mewitz | 358/160 |
| 4,606,064 | 8/1986 | Haendle | 378/99 |
| 4,618,990 | 10/1986 | Sieb et al. | 382/43 |
| 5,054,045 | 10/1991 | Whiting et al. | 378/99 |
| 5,117,446 | 5/1992 | Haaker et al. | 378/99 |

OTHER PUBLICATIONS

*Multiple-Target Tracking with Radar Applications*, pp. 19–20, S. S. Blackman, 1986.

Primary Examiner—David P. Porta
Attorney, Agent, or Firm—Quarles & Brady

[57] ABSTRACT

An x-ray fluorographic system which produces a cineangiogram enables a feature in the image to be identified with a cursor and automatically tracked in subsequent images. The identified feature, such as a suspected lesion in a coronary artery, is located in each x-ray frame of the cineangiogram and the data is displayed such that the feature remains motionless in the center of each successive image.

9 Claims, 3 Drawing Sheets

DIGITAL X-RAY IMAGING SYSTEM WITH AUTOMATIC TRACKING

BACKGROUND OF THE INVENTION

The field of the invention is digital x-ray imaging systems, and particularly, x-ray fluorographic systems used in clinical cardiology to view cardiac vessel lesions.

In x-ray fluorographic systems the x-rays are received by an image intensifier which converts them to a bright optical image that appears on an output phosphor of the intensifier tube. This image is viewed with a video camera which converts the image to analog video signals, and these are digitized into frames of picture elements (pixels). These frames of digitized x-ray data are typically processed in a digital video processor to filter out undesired signals and enhance desired features. The resulting image data is then applied to a digital-to-analog converter which produces a video signal suitable for driving a CRT monitor.

The digitized frames of image data may be used in a number of ways by a cardiologist. As indicated above, the frames can be displayed immediately on the CRT monitor to provide the cardiologist with a cineangiogram or fluoroscopic view of the patient in real time. Such a mode of operation may be used, for example, when positioning a catheter in the patient's vascular system for treatment of a lesion. This mode requires that any processing performed by the digital video processor be carried out at a frame rate which does not cause the picture to flicker.

In the alternative, the acquired image frames may also be stored and played back by the cardiologist. For example, a series of image frames may be acquired for a complete cardiac cycle, digitized and stored. This series of image frames may be processed in a variety of ways to enhance specific features and then played back on the CRT monitor. The cardiologist may play the processed series of image frames back in real time to observe the vasculature during an entire cardiac cycle, he may step through each frame, or he may freeze the sequence on a particular image frame. These "off-line" modes of operation are employed primarily for location and diagnosis of lesions prior to any remedial procedure.

Current digital cardiovascular x-ray systems utilize digital image processing techniques to zoom and pan both static and dynamic cardiac images. In most cases, a statically zoomed image provides the most clinical information about cardiac vessel structure and composition. However, dynamic loops comprised of a series of x-ray frames yield valuable clinical information when played in real time or slow motion. When viewing such cineangiograms an interpolated image sequence provides increased spatial resolution, however, the cardiac motion forces the cardiologist to "track" the moving lesion or vessel. This movement not only distracts the cardiologist, but it also may force the doctor to slow the loop display rate or use a single-step mode. The problem is further complicated when the lesion or vessel of interest, moves in front of or behind other vessels during the cardiac cycle.

A solution to this problem is disclosed in U.S. Pat. No. 5,054,045 entitled "Coronary Tracking Display." In this system the cardiologist identifies a region in the first frame of the cineangiogram, and this region is tracked during each subsequent frame and made to remain stationary on the display screen. A vessel or lesion can thus be identified and easily followed during the play back of the cineangiogram loop. Other surrounding features are caused to move, but the identified region of interest remains stationary. In one embodiment the cardiologist examines each frame manually and identifies with a screen cursor the feature of interest to be followed. In the alternative, the feature of interest can be identified in the first frame and a means for automatically locating that same feature in subsequent frames may be employed. Although a number of techniques for automatically locating an identified feature in a set of x-ray images are suggested in the prior art, none provide a means which operates automatically and satisfactorily at real time in a commercially viable system.

SUMMARY OF THE INVENTION

The present invention relates to a digital cardiovascular x-ray system, and particularly to a system which will produce a cineangiogram in which an identified feature in one frame is automatically tracked in subsequent frames and a series of images is produced in which the identified feature remains substantially stationary. More particularly, the invention includes means for acquiring a series of digitized x-ray images which depict anatomical features in a corresponding series of physical positions, means for identifying one of the anatomical features in a first of the digitized x-ray images, means for automatically locating the identified anatomical feature in each of the subsequent digitized x-ray images, and means for displaying a portion of each digitized x-ray image in which the located anatomical feature in each digitized x-ray image is positioned in the center of the display such that it is magnified and remains substantially motionless during the sequential display of the series of x-ray images. The invention is characterized by extracting a search kernel from the prior x-ray frame centered on the identified feature located in the prior x-ray frame, extracting a tracking window from the current x-ray frame centered on the identified feature located in the prior x-ray frame, filtering both the search kernel and the tracking window to enhance the edges of features depicted therein, finding the current location of the identified feature by locating the peak correlation between the search kernel and the tracking window, extracting an array of image data from the current x-ray frame which is centered on the current location of the identified feature, and producing a display using the array of image data.

A general object of the invention is to provide a system which will automatically track an identified feature which moves in a series of x-ray frames. The operator identifies the location of a feature to be tracked in a first x-ray frame and the system automatically locates that feature in subsequent frames. These locations are then used to produce a corresponding series of images in which the located feature is centered and remains substantially stationary.

Another object of the invention is to provide an automatic tracking system which can be constructed using commercially available devices. The extraction, filtering, correlation and display functions can be carried out using commercially available digital signal processing components.

Another object of the invention is to provide an automatic feature tracking system which can operate in real time. The extraction, filtering, and correlation functions are relatively simple functions which can be carried out quickly by digital signal processing circuits operating at normal clock rates. The correlation operation is simplified by subtracting the mean value of the search kernel and the tracking window from their respective pixel values prior to correlation. The correlation operation is then a series of subtraction and counting operations.

A more specific object of the invention is to accurately track the location of a moving feature in a series of x-ray frames. The accuracy of the correlation operation is significantly improved by filtering the search kernel and tracking window data to enhance the edges of features depicted therein. In the case of coronary arteries, for example, a Robert's operation is employed as the filter and significantly improves the tracking of coronary arteries.

Another more specific object of the invention is to provide the operator with a number of ways in which the tracked feature is displayed. The extracted array of image data may be displayed directly or preferably it is magnified to zoom in on the identified feature. The extracted array of image data may be displayed alone, or it may overlay the display of the frames of x-ray data. To block distracting features which might otherwise appear on the display, a dark mask can be configured to reveal only the identified feature and immediately surrounding tissues.

Yet another specific object of the invention is to provide the operator with a novel display of a sequence of x-ray frames in which features of interest remain stationary. A sequence of x-ray frames are processed according to the present invention and stored for later, off-line, analysis. A palindrome mode of display is provided in which the sequence of images is played back in the forward order and then the reverse order in repetitive cycles. This insures that moving features do not drastically jump from one position to another during the cycle, as would occur if the sequence is repetitively played back in the forward direction.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENTS

Figure 1:
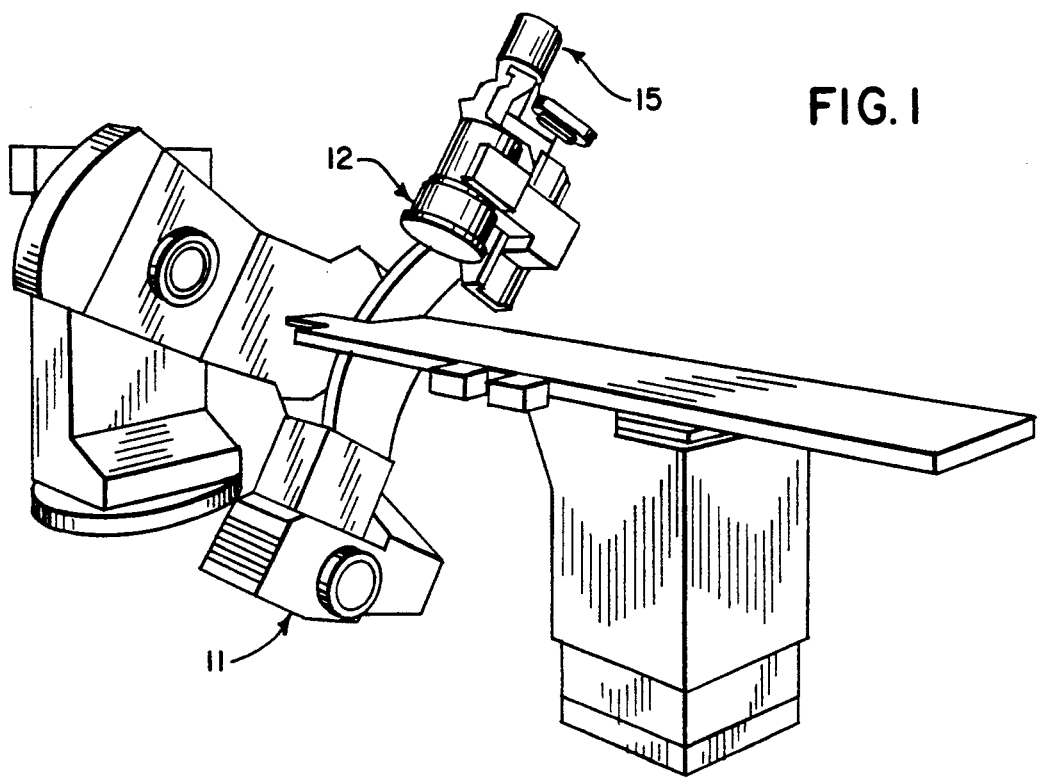
FIG. 1 is a pictorial view of a digital cardiovascular x-ray system which employs the present invention.
Figure 2:
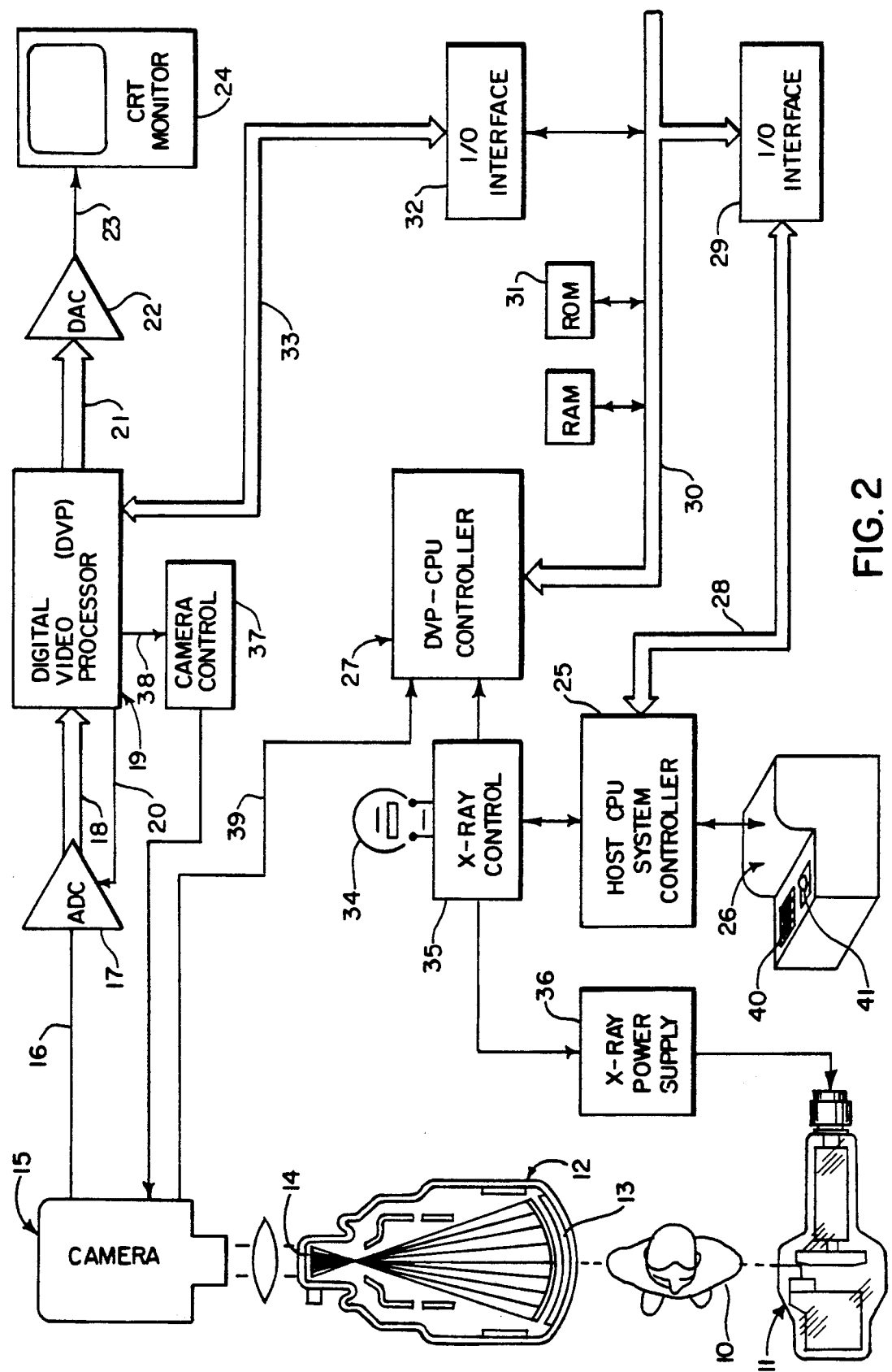
FIG. 2 is a schematic drawing of the digital cardiovascular x-ray system of FIG. 1.

The basic elements of a typical system for acquiring digital fluorographic images is depicted in FIGS. 1 and 2. The patient who is to undergo a fluorographic examination is shown at 10. An x-ray source 11 is located to one side of the patient and is controllable to project an x-ray beam through the patient for producing an x-ray image. An image intensifier 12 is positioned on the opposite side of the patient 10. The x-ray image emergent from the patient impinges on the input phosphor 13 of the intensifier 12 which is operative to convert the light on input phosphor 13 to a modulated electron beam image which impinges on an output phosphor 14 where conversion to a bright optical image occurs.

The optical image on output phosphor 14 is viewed with a video camera 15 that converts the image to corresponding analog video signals. The analog video signals are output from the camera 15 on line 16 and are input to an analog-to-digital converter (ADC) 17. ADC 17 is operative to convert the analog signal for each horizontal line to a series of digital signals whose values correspond to the intensities of the picture elements (pixels) comprising the x-ray image. The horizontal lines of digital pixel data are fed by way of bus 18 to a digital video processor (DVP) 19, where the lines forming a complete x-ray image frame are stored in a memory. In the most advanced fluorographic systems the digital pixel data representing each image frame are stored in raw form so the original data can be accessed at any time by the DVP 19 for further processing. DVP 19 provides a 12 MHz sample clock by way of line 20 to the ADC 17.

After the x-ray image data is processed in DVP 19, the digital image data signal is fed from the DVP 19 by way of bus 21 to the input of a digital-to-analog converter (DAC) 22 and converted to analog video signals. The analog video signals are supplied, by way of a line 23 to a CRT monitor 24 on whose screen the image is displayed. Each frame of x-ray image data is processed as it is produced by the camera 15 and may be displayed on the CRT screen 24 immediately to provide real-time display of the subject. In the alternative, a sequence of x-ray frames may be acquired and stored for later playback and analysis.

The present invention is carried out in part by the DVP 19. The DVP 19 includes several electronic components such as two full frame digital memories, an arithmetic logic unit (ALU), multiplexers, registers and multipliers which are interconnected by data buses, and input buses for raw or reprocessed images and an output line 21 for image signals leading to the CRT monitor on which a fluorographic image is viewed. A digital video processor central processor unit (DVP-CPU) 27 provides control data to the various components of the DVP 19 to activate or deactivate them for an image processing step or steps which, in effect, means that the data paths, data sources and data destination are addressed and controlled by instructions or signals provided by the DVP-CPU 27. Thus, the DVP 19 can be adapted within television frame rates to do such operations as adding and subtracting digital images, or shifting an image. The DVP 19 can also be controlled to multiply image pixel data by selected coefficients as required for various processing steps. A digital video processor such as that described in Andrews et al U.S. Pat. No. 4,449,195 is preferred, and the entire disclosure is incorporated herein by reference. The Andrews et al patent is assigned to the assignee of this application for patent.

The fluorographic system in FIG. 2 is controlled overall by a host central processor unit (CPU) system controller 25. An operator terminal 26 allows the examining cardiologist to call up any of a number of available fluorographic techniques allowing visualization of a particular part of the patient. The host CPU 25 sends generalized instructions to the DVP-CPU identifying the image acquisition procedure for the elected type of examination. These instructions are provided over address/data bus 28, I/O interface 29 and bus 30. DVP-CPU 27 in turn accesses a recipe or list of instructions, for executing the examination technique, from read-only memory (ROM) 31 and through I/O interface 32 and bus 33 delivers the proper control words to the registers of the components in the DVP 19 so the components are activated and deactivated at the proper times and the data paths in the DVP 19 are properly routed to execute the image acquisition and processing instructions.

A sequence of x-ray exposures is initiated by actuating a hand switch 34. The x-ray control circuits 35 respond by turning the x-ray source 11 on an off at the proper times to start and stop individual exposures. A video camera control 37 receives timing signals from a DVP clock, by way of line 38 and a time base for the DVP-CPU controller 27 is produced by the vertical blanking pulse from video camera 15 as supplied over line 39.

In addition to providing a keyboard 40, the operator terminal 26 provides a trackball 41. The trackball 41 can be rotated in all directions to move a bright cursor on the CRT monitor 24. As described in U.S. Pat. Nos. 4,245,244 and 4,454,507, which are owned by the assignee of this application, such graphics, or cursor generators are well known in the art and they produce a series of pulses which correspond to the x,y coordinates of the cursor on the monitor's screen. The cursor coordinate information is applied to the host CPU 25, which in turn supplies it to the DVP 19 for use as will be described in more detail below.

Figure 3:
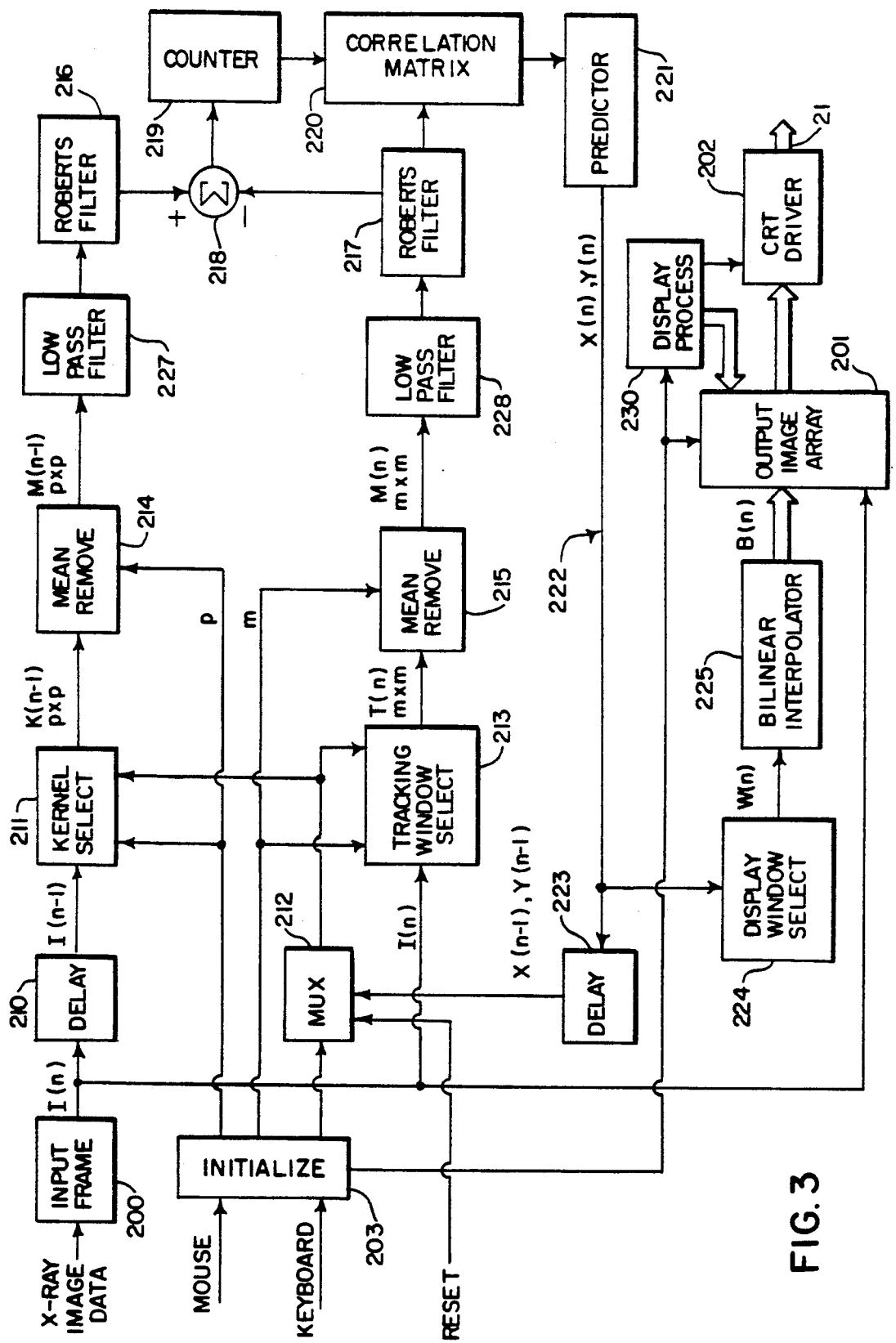
FIG. 3 is a block diagram of the adaptive feature tracking filter of the present invention which is part of the digital video processor in FIG. 2.

Referring particularly to FIG. 3, the functions carried out by the DVP 19 in response to the recipe executed by the DVP-CPU controller 27 to produce a cineangiogram according to the present invention are shown in block diagram form. The series of digitized x-ray frames are received at a frame buffer memory 200 and are processed as will now be described to produce a corresponding series of digitized x-ray frames at output 21. In the following description, the index "n" refers to the current digitized x-ray frame being processed in the series and the n-1 frame refers to the previously processed x-ray frame in the series. As each x-ray frame is received it is applied directly to an output image array 201. If the automatic tracking feature is not enabled, therefore, the series of digitized x-ray frames is simply passed through the DVP 19 and applied to a CRT driver 202 which controls the DAC 22 and CRT monitor 24 to sequentially display each image in real time as it is received. When the automatic tracking feature is enabled by the operator, it is initialized at 203 by inputting the location ($x_0,y_0$) of the feature to be tracked.

Figure 4:
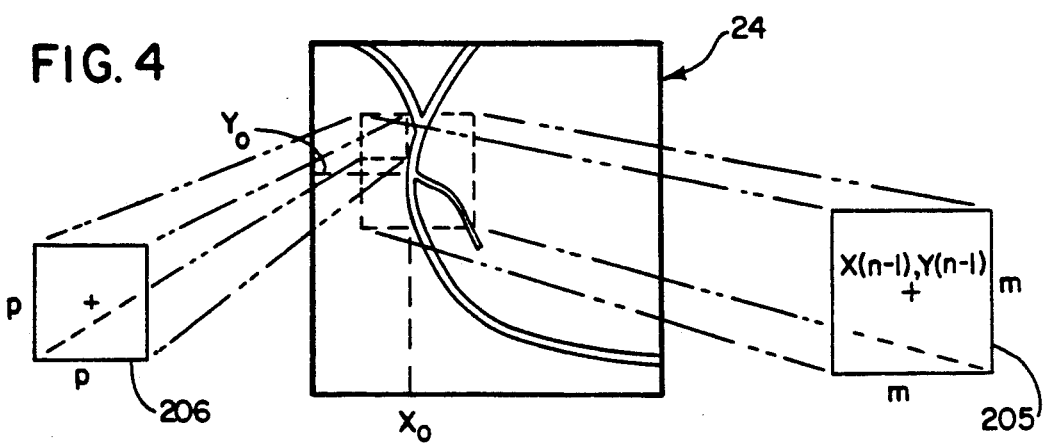
FIG. 4 is a schematic representation of an image showing a search kernel and a tracking window which are constructs used to implement the present invention.

FIG. 4 is a schematic drawing of the CRT screen 24 showing an image to be tracked as well as two constructs used to perform the tracking. One of these constructs is a tracking window 205 which is an m by m pixel sample of the current x-ray frame data I(n) centered on the last known location of the feature to be tracked. At initialization, this location is the cursor location $x_0,y_0$ produced by the trackball 41. In subsequent frames (n) the tracking window is centered on the feature location $x(n-1)$, $y(n-1)$ as determined in the previous frame $(n-1)$. The size of the tracking window 205 is configured as a tracking parameter m, and in the preferred embodiment which produces a 512 by 512 pixel display, a value of m=81 is used. The tracking window 205 determines the area in which a search will be made in the current x-ray frame I(n) for the identified feature. If the tracking window 205 is too small, the feature may move outside the m by m area defined by the tracking window between the acquisition of successive x-ray frames, and if it is too large, the search will take too long.

The other construct used to automatically track the identified feature is a search kernel 206, which is a p by p pixel sample of the previous x-ray frame data $I(n-1)$ centered about the previously identified feature location $x(n-1)$, $y(n-1)$. The size of the search kernel 206 is configured as the tracking parameter p, and in the preferred embodiment, p is set to a value of 41. As will be explained in detail below, the location of the identified feature in the current x-ray frame I(n) is accomplished by finding the location within the tracking window 205 where the data in the search kernel 206 correlates best with the corresponding data in the tracking window 205. In other words, the search kernel 206 is moved around within the tracking window 205 until the best match is found. This location $x(n)$, $y(n)$ is the calculated current position of the feature being tracked.

Referring again to FIG. 3, after each x-ray frame of data I(n) is processed, it is saved in a delay 210 and is available during the next frame as the previous frame data $I(n-1)$. From this previous data $I(n-1)$ the p by p pixel search kernel 206 is selected at block 211. The center of the search kernel 206 is provided by a multiplexer 212 which is controlled by a reset input to select either the initialized feature location values $x_0,y_0$ or the calculated values $x(n-1)$, $y(n-1)$ from the previous frame. The search kernel 206 is output as a p by p array of data $K(n-1)$.

The tracking window 205 is extracted from the current x-ray frame data I(n) at block 213. The tracking window select 213 receives the tracking parameter m which determines its size, and it receives the last known feature location from the multiplexer 212 which determines its center point. The tracking window is output as an m by m array of data T(n).

To simplify the computations necessary to correlate the search kernel 206 with the tracking window 205 the mean value of the elements in each array are subtracted therefrom. As indicated by block 214 the mean value of the elements in the search kernel array $K(n-1)$ is calculated, and then this mean value is subtracted from each element in the search kernel 206 to produce a p by p element array $M(n-1)$. As indicated by block 215, a similar function is performed on the tracking window data T(n) to produce an m by m element array M(n). This mean remove function is used to simplify the amount of multiplication required in the correlation function. The simplification occurs in the denominator term of the correlation. This term is proportional to the variance of the random variables. The number of operations required to perform the variance of a zero mean process is much less than the number of operations required for a non-zero mean random variable, i.e.:

$$\sqrt{[x - \mu_x^2][y - \mu_y^2]} = \sqrt{E[x^2]E[y^2]}$$

when $\mu_x \mu_y = 0$.

To improve the automatic tracking function, both the tracking window data M(n) and the search kernel data M(n−1) are filtered to reduce noise. Accordingly, as indicated by blocks 227 and 228 the tracking window data is applied to a low-pass filter and the search kernel data is applied to a low-pass filter. The low-pass filters 227 and 228 are conventional box car average filters which employ a 5 by 5 filter kernel to smooth the data.

In order to improve the correlation and the resulting tracking function, both the tracking window data M(n) and the search kernel data M(n−1) are further filtered to enhance the edges of features. The filter which is particularly useful in enhancing the edges of cardiac vessels is the Robert's filter operator. As indicated by block 216 each value $p_{ij}$ in the search kernel data array M(n−1) is replaced with a filtered value $R_{ij}$, where $R_{ij}$ is calculated as follows:

$$R_{i,j} = |p_{i,j} - p_{i+1,j+1}| + |p_{ij+1} - p_{i+1,j}|$$

Similarly, as indicated by block 217, each value $m_{ij}$ in the tracking window data array M(n) is replaced with a filtered value $r_{ij}$, where $r_{ij}$ is calculated as follows:

$$r_{ij} = |m_{ij} - m_{i+1,j+1}| + |m_{i,j+1} - m_{i+1,j}|$$

The two filtered arrays M(n−1) and M(n) are now in condition for correlation.

The correlation is performed by an iterative process in which the smaller search kernel 206 is moved to successive positions within the larger tracking window 205 and the corresponding array elements are subtracted as indicated at 218. At each position of the search kernel 206, the number of zeros that result from the subtraction process are counted at block 219 and stored in a correlation matrix 220 along with the x,y position of the search kernel center point. After the search kernel 206 has been moved to all possible positions within the confines of the tracking window 205, the correlation matrix 220 is examined to determine the location where the maximum number of zeros were found. This is the calculated new position of the tracked feature.

While the output of the correlator is usually used as the position x(n), y(n) of the tracked feature in the current x-ray frame I(n), a check is made against a predicted location by a predictor 221. The predictor 221 stores the values of the tracking point from the three previous x-ray frames n−1, n−2 and n−3.

Using these values, it calculates a predicted value of the current tracking position and a radius within which it would expect to find the actual tracking position x(n), y(n). If the actual tracking position is not within this radius, the predicted value is substituted and output at 222 as the current position x(n), y(n). For a more detailed description of how the predictor 221 operates, reference is made to chapter 2 of the book by Samuel S. Blackman entitled "Multiple-Target Tracking With Radar Applications" published in 1986 by Artech House, Inc.

The current position x(n), y(n) of the tracked feature is stored in a delay 223 for use in the processing of the next x-ray frame, and it is used by a display window select 224 to locate the center of the x-ray image array W(n) to be extracted from the current x-ray frame data I(n). In the preferred embodiment a 256 by 256 pixel array of data W(n) centered on the current track position x(n), y(n) is extracted from the 512 by 512 x-ray frame I(n). Any points in W(n) lying outside the 512 by 512 array I(n) are set to zero and are black. The extracted array W(n) is then applied to a bilinear interpolator 225 which doubles its size by magnifying the 256 by 256 pixel image array W(n) to produce a 512 by 512 pixel image array B(n). The net effect is to zoom in on the tracked feature and magnify it and the surrounding structures by a factor of two. The resulting image array B(n) is applied to the output image array 201 which is displayed on the CRT monitor 24 by the CRT driver 202.

There are many variations in the way the tracked feature is displayed. For example, a smaller array W(n) can be extracted by the display window select 224 and the magnification need not be limited to two. Also, a small display window W(n) can be extracted, and rather than fill the entire screen with a magnified version, it may be displayed concurrently with the unprocessed x-ray frame I(n). For example, the entire x-ray frame I(n) is stored in the output image array 201 and the smaller display window W(n) with centered feature may be stored so as to appear in one corner of the combined images. The cardiologist may thus see all the structures in the field of view of the x-ray system as they move during the cardiac cycle, and at the same time, view a magnified window in which the identified feature remains centered and stationary during the cardiac cycle.

Another feature which is very helpful in viewing the magnified image B(n) is to employ a mask which blocks portions of the image that may be a distraction to the cardiologist. For example, because the tracked feature is always centered in the image B(n), features which are normally stationary, such as the dark regions at the boundary of the x-ray system's field of view, will move and can be very distracting as they move in and out of the magnified image B(n). To block these distractions the operator can configure a display processor 230 to produce a dark mask that appears around the periphery of the CRT display 24. The diameter of the resulting circular opening in this mask can be set so that the cardiologist can see the structures of interest while unimportant, or distracting, structures are masked over. The implementation of this mask feature is described in U.S. Pat. No. 4,571,619 which is owned by the assignee of this application and which is incorporated herein by reference.

In the above-described modes of operation the display process 230 is configured by the operator to display each processed x-ray frame in real-time as it is acquired. This fluoroscopic mode of operation is used most often to assist the cardiologist as he is carrying out a procedure such as coronary angioplasty. However, the display process 230 can also be configured to store the sequence of processed x-ray frames so that they can be played back at a later time for careful diagnosis. For example, a series of x-ray frames may be acquired to show the patient's heart during an entire cardiac cycle. The sequence of frames is then read out of the output image array 201 by the display process 230 in real time, slow motion or step-by-step so that the cardiologist can carefully follow the changes that occur in a particular coronary artery. Not only can the particular coronary artery be rendered motionless and magnified according to the present invention, but the sequence can be viewed in a palindrome mode. In this mode the display process 230 reads out the sequence to depict the cardiac cycle. Instead of repeating the same sequence again, however, the display process 230 then reads out and displays the sequence of x-ray frames in reverse order. While such reverse playback does depict the coronary cycle in reverse, such palindrome playback avoids the discontinuity in feature positions that occur when the sequence is reset to repeat in the forward direction. As a result, moving structures about the centered feature move smoothly at all times during the playback without periodic jumps in their position. As with the mask feature described above, the palindrome mode eliminates yet another distraction for the cardiologist.

We claim:

1. In a digital x-ray system which produces a sequence of x-ray frames, a method for automatically displaying the sequence of x-ray frames which comprises:

identifying a feature depicted in the first of the x-ray frames;

for each subsequent x-ray frame in the sequence;

a) extracting a search kernel from the prior x-ray frame which is an array of pixel values centered on the identified feature located in the prior x-ray frame;

b) extracting a tracking window from the current x-ray frame which is an array of pixel values centered on the identified feature located in the prior x-ray frame;

c) filtering the data in both the search kernel and the tracking window to enhance the edges of features depicted therein;

d) finding the location of the identified feature in the current x-ray frame by locating the peak correlation between the search kernel and the tracking window;

e) extracting an array of image data from the current x-ray frame which is centered on the current location of the identified feature; and f) producing a display using the array of image data.

2. The method as recited in claim 1 in which the filtering of the search kernel and the tracking window is performed by applying a Robert's operation to each pixel value therein.

3. The method as recited in claim 1 in which the peak correlation between the search kernel and the tracking window is performed by subtracting pixel values in the search kernel from corresponding pixel values in the tracking window and determining the position of the search kernel relative to the tracking window which produces the maximum number of zero results from the subtraction step.

4. The method as recited in claim 1 in which the mean value of the pixel values in the search kernel is calculated and this mean value is subtracted from each pixel value therein, and the mean value of the pixel values in the tracking window is calculated and this mean value is subtracted from each pixel value therein.

5. The method as recited in claim 1 in which the display is produced by magnifying the array of image data.

6. The method as recited in claim 1 in which the display is produced by combining the array of image data with the current x-ray frame.

7. The method as recited in claim 1 in which the display is produced by combining the array of image data with a mask which blocks some features depicted in the array of image data from view.

8. The method as recited in claim 1 in which the array of image data int he sequence is stored and the stored arrays of image data are displayed in a palindrome mode in which they are cyclically displayed in the sequence they were acquired and in the reverse sequence they were acquired.

9. A method of displaying a sequence of x-ray frames, the steps comprising:

digitally processing each x-ray frame in the sequence so that an identified feature therein is displayed at a substantially fixed location on a display screen;

magnifying each digitally processed x-ray frame; and displaying each magnified and digitally processed x-ray frame in a palindrome mode in which they are cyclically displayed in the sequence they were acquired followed by the reverse sequence they were acquired.

* * * * *